United States Patent [19]
Doherty et al.

[11] Patent Number: 4,465,687
[45] Date of Patent: Aug. 14, 1984

[54] THIENAMYCIN DERIVATIVES AS ANTI-INFLAMMATORY AGENTS

[75] Inventors: James B. Doherty, New Milford; Morris Zimmerman, Watchung; Bonnie M. Ashe, Westfield, all of N.J.

[73] Assignee: Merck & Co., Inc., Rahway, N.J.

[21] Appl. No.: 381,280

[22] Filed: May 24, 1982

[51] Int. Cl.$^3$ .................. A61K 31/40; A61K 31/695
[52] U.S. Cl. .................................. 424/274; 424/184
[58] Field of Search ............................ 424/274, 184

[56] References Cited

U.S. PATENT DOCUMENTS 3,546,211  12/1970  Base .................................. 260/239

FOREIGN PATENT DOCUMENTS 1570980  7/1980  United Kingdom .

Primary Examiner—Stanley J. Friedman
Attorney, Agent, or Firm—Theresa Y. Cheng

[57] ABSTRACT

N-acyl-derivatives of thienamycin esters are found to be potent elastase inhibitors and therefore are useful anti-inflammatory agents.

5 Claims, No Drawings

THIENAMYCIN DERIVATIVES AS ANTI-INFLAMMATORY AGENTS

BACKGROUND OF THE INVENTION

We have found that esters of N-acyl derivatives of thienamycin are potent elastase inhibitors and therefore are useful anti-inflammatory agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, osteoarthritis, spondylitis, lupus, psoriasis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme able to hydrolyze the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory dieseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allows them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitryspin, either genetic or due to oxidants, has been associated with pulmonary emphysema which is a disease characterized by a progressive loss of long elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, New York, 1949, pp. 196–206.

Accordingly, an object of this invention is to discover new protease inhibitors, especially elastase inhibitors, useful for controlling tissue damage and various inflammatory conditions mediated by proteases particularly elastase.

Another object of the present invention is to provide pharmaceutical compositions for the administration of these protease inhibitors, i.e., the active N-acyl thienamycin esters.

Still a further object of this invention is to provide a method of controlling inflammatory conditions by administering a sufficient amount of the N-acyl thienamycin esters in a mammalian species in need of such treatment.

DETAILED DESCRIPTION OF THE INVENTION

This invention relates to esters of known N-acyl thienamycin derivatives as potent elastase inhibitors useful in the prevention, control and treatment of inflammatory conditions especially arthritis and emphysema.

Some of the N-acyl thienamycin free acids are known antibiotics which have been described in Great Britain Pat. No. 1,570,986 (wherein A and B in Formula I below are both hydrogen) published on July 9, 1980.

The N-acyl thienamycin esters of the present invention may be depicted by the following generic structural formula (I):

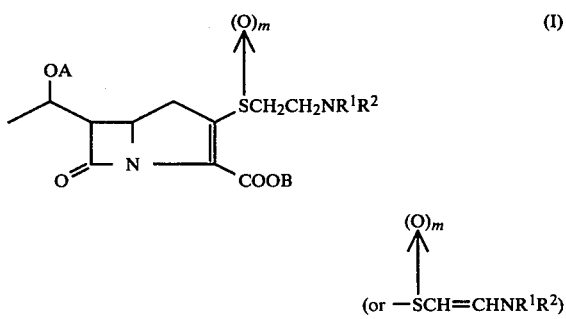

(or —SCH=CHNR$^1$R$^2$)

wherein m is 0 to 2; R$^1$ and R$^2$ independently are hydrogen, loweralkyl or an acyl group. In addition, R$^1$ and R$^2$, when it is feasible, may join together and form a cyclic diacyl group such as phthaloyl. The term "acyl" includes not only carboxylic acyl, but also its thio analogues in which the carbonyl oxygen is replaced by sulphur; diacyl radicals in which R$^1$ and R$^2$ are joined together; and acyl radicals from sulfur and phosphorus acids, such as substituted sulfonyl, sulfinyl and sulfenyl radicals and substituted P (III) and P(V) radicals such as the substituted phosphorous, phosphoric, phosphonous and phosphonic radicals.

In the generic representation of the compounds of the present invention (I, above), the acyl radical represented by either R$^1$ and R$^2$ can, inter alia, be a substituted or unsubstituted aliphatic, aromatic, heterocyclic, araliphatic or heterocyclylaliphatic carboxylic acid radical, a substituted or unsubstituted carbamyl radical or a carbothioic acid radical. One group of acyl radicals can be represented by the general formula:

where X is O or S and R" represents hydrogen; amino; substituted amino such as C$_{1-6}$ alkylamino or di(C$_{1-6}$ alkyl) amino in which the alkyl radicals(s) are substituted or unsubstituted; straight or branched-chain C$_{1-6}$ alkyl; mercapto, substituted mercapto such as alkylthio, typically comprising 1 to 6 carbon atoms, or arylthio, typically comprising 6 to 10 carbon atoms; hydroxy; substituted hydroxy such as alkoxy, typically comprising 1 to 6 carbon atoms, or aryloxy, typically comprising 6 to 10 carbon atoms; alkenyl or alkynyl, typically comprising 2 to 6 carbon atoms; aryl, such as phenyl; aralkyl, such as benzyl; cycloalkyl, typically comprising 3 to 6 carbon atoms; or a heteroaryl or heteroaralkyl group (mono- and bicyclic) in which the alkyl residue (if any) typically comprises 1 to 3 carbon atoms and the heterocyclic ring typically comprises 4 to 10 atoms and the hetero atom or atoms is/are preferably O, N and/or S; such above-listed groups can be unsubstituted or can be substituted by radicals such as OH, SH, SR$^8$ (R$^8$ is C$_{1-6}$ alkyl or aryl such as phenyl), alkyl or alkoxy groups having 1 to 6 carbon atoms, halogens such as Cl, Br, F or I, cyano, carboxy, sulfamino, carbamoyl, sulfonyl, azido, amino, substituted amino, such as (C$_{1-6}$ alkyl)-substituted amino including quaternary ammonium, C$_{1-6}$ halogenated alkyl such as trifluoromethyl, carboxy (C$_{1-6}$ alkyl), carbamoyl (C$_{1-6}$ alkyl), N-substituted carbamoyl (C$_{1-6}$ alkyl), amidino, guanidino, N-substituted guanidino, guanidino-(C$_{1-6}$ alkyl) or nitro. Representative examples of such acyl groups that might be mentioned are those in which R" is benzyl, p-hydroxybenzyl, 4-amino-4-carboxybutyl, methyl, (in which case, when X is O, the acyl radical is acetyl), cyanomethyl, 2-pentenyl, n-amyl, n-heptyl, ethyl, 3- or 4-nitrobenzyl, phenethyl, β, β-diphenylethyl, methyldiphenylmethyl, triphenyl-methyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromo-benzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-amino-cyclohexyl, 2- and 3-thienylaminoethyl, 2-(5-nitrofuranyl)vinyl, phenyl, o-methoxphenyl, o-chlorophenyl, o-phenylphenyl, p-aminomethylbenzyl, 1-(5-cyanotriazolyl)methyl, difluoromethyl, dichloromethyl, dibromomethyl, 1-(3-methyl-imidazolyl)methyl, (2 or 3)-(5-carboxymethylthienyl)methyl, (2 or 3)-(4-carbamoylthienyl)methyl, (2 or 3)-(5-methylthienyl)methyl, (2 or 3)-(methoxythienyl)methyl, (2 or 3)-(4-chlorothienyl)-methyl, (2 or 3)-(5-sulfothienyl)methyl, (2 or 3)-(5-carboxythienyl)methyl, 3-(1,2,5-thiadiazolyl)-methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, tetrazolylmethyl, benzamidinomethyl and cyclohexyl-amidinomethyl.

The acyl group can also be a radical of the formula:

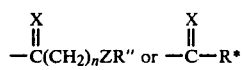

where X is O or S; n is 0, 1, 2, 3 or 4; Z is oxygen, sulfur, carbonyl or imino; R" is as defined as above, except that when Z is oxygen R" is not mercapto or hydroxy, when Z is sulfur R" is not amino or hydroxy, and when Z is imino R" is not mercapto; and R* is as defined below. Representative members of the substituent

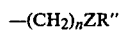

that might be mentioned are allylthiomethyl, phenylthiomethyl, butylthiomethyl, α-chlorocrotylthiomethyl, phenoxymethyl, phenoxyethyl, phenoxybutyl, phenoxybenzyl, phenoxyphenoxymethyl, (dimethylmethoxy)methyl, (dimethylbutoxy)methyl, (dimethylphenoxy)methyl, 4-guanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)phenoxymethyl, 2-pyrimidinylthiomethyl, phenethylthiomethyl, 1-(5,6,7,8-tetrahydronaphthyl)oxymethyl, N-methyl-4-pyridylthio, benzyloxy, methoxy, ethoxy, phenoxy, phenylthio, amino, methylamino, dimethylamino, a pyridinium methyl or trimethylammonium-methyl non-toxic salt, cyanomethylthiomethyl or trifluoromethylthiomethyl. R is 4-pyridylethyl, 4-pyridylpropyl, 4-pyridylbutyl, 3-imidazolylethyl, 3-imidazolylpropyl, 3-imidazolylbutyl, 1-pyrrolylethyl, 1-pyrrolylpropyl and 1-pyrrolylbutyl.

Alternatively, the acyl group can be a radical of the formula:

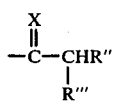

where R" as defined as above and R''' is azido, carbamoyl, guanidino, amidino, acyloxy, halo, namely Cl, F, Br, I, sulfamino, tetrazolyl, sulfo, carboxy, carbalkoxy, phosphono, alkoxy or arylthio. Representative members of the substituent

that might be mentioned are α-aminobenzyl, α-amino(2-thienyl)methyl, α-(methylamino)benzyl, α-aminomethylthiopropyl, α-amino-(3 or 4)-chlorobenzyl, α-amino-(3 or 4)-hydroxybenzyl, α-amino-2,4-dichlorobenzyl, α-amino-3,4-dichlorobenzyl, D(−)-α-hydroxybenzyl, α-carboxybenzyl, α-amino-(3-thienyl)-methyl, D(−)-α-amino-3-chloro-4-hydroxybenzyl, α-amino(cyclohexyl)methyl, α-(5-tetrazolyl)benzyl, 2-thienyl-carboxymethyl, 3-thienyl-carboxymethyl, 2-furyl-carboxymethyl, 3-furyl-carboxymethyl, α-sulfaminobenzyl, 3-thienyl-sulfaminomethyl, α-(N-methylsulfamino)benzyl, D(−)-2-thienyl-guanidinomethyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiozolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)carboxy-methyl, 3-(1,2-thiazolyl)-aminomethyl, 3-(1,2-thiazolyl)hydroxymethyl, 3-(1,2-thiazolyl)carboxymethyl, 2-(1,4-thiazolyl)-aminomethyl, 2-(1,4-thiazolyl)hydroxymethyl, 2,-(1,4-thiazolyl)-carboxymethyl, 2-benzothienylaminomethyl, 2-benzothienylhydroxymethyl, 2-benzothienylcarboxymethyl, α-sulfobenzyl or α-phosphonobenzyl. The acyl radical can also be α-diethylphosphono or α-monoethylphosphono. Further acyl radicals of interest when X=oxygen are:

where R3' and R4' are as defined below. R3' represents hydrogen, chloro, fluoro, bromo, iodo, amino, guanidino, phosphono, hydroxy, tetrazolyl, carboxy, sulfo or sulfamino and R4' represents phenyl, substituted phenyl, a mono- or bicyclic heterocyclyl containing one or more oxygen, sulfur or nitrogen atoms in the ring, (such as furyl, quinoxalyl, thienyl, quinolyl, quinazolyl, thiazolyl, isothiazolyl, tetrazolyl, oxadiazolyl or thiadiazolyl), phenylthio, phenyloxy, alkyl of 1–6 carbon atoms, heterocyclic-thio or substituted heterocyclicthio groups; or cyano. The substituents on the residues, R3' and R4', can be halo, carboxymethyl, quanidino, quanidinomethyl, carboxyamidomethyl, aminoethyl, nitro, methoxy or methyl. When R3' is hydrogen, hydroxy, amino or carboxy and R4' is phenyl or a (5 or 6)-membered heterocyclic ring having one or two sulfur, oxygen or nitrogen hetero atoms such as tetrazolyl, thienyl, furyl and phenyl, the following acyl radicals are representative; phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The substituents R1, R2 and if appropriate R3' may also be selected from sulphur (1) and phosphorus (2) radicals:

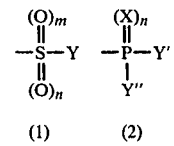

in which with respect to (1), each of m and n is 0 or 1 and Y is O⊖M⊕, —N(R")2, or R"; where M⊕ is hydrogen, an alkali metal cation, an alkaline-earth metal cation or an organic base; and R" is as defined above, e.g., alkyl, alkenyl, aryl or heteroaryl.

With respect to (2), X is 0 or S; n is 0 or 1; and each of Y' and Y", independently of the other, is O⊖M⊕, —N(R")2, —R" or —ZR" where all symbols are as defined above, e.g., R" and ZR" may be alkyl, alkenyl, aryl or heteroaryloxy, or Y' and Y", including R" residues, are joined together to form cyclic ester, ester-amide and amide functions. Illustrative examples of compounds containing R1 and/or R2 having the formula (1) are N-(methylsulfonyl)thienamycin, N-(o-nitrophenylsulfonyl)thienamycin, N-(p-chlorophenylsulfinyl)thienamycin, N-(o-nitro-phenylsulfenyl)thienamycin, N-sulfamoylthienamycin, N-dimethylsulfamoylthienamycin and thienamycin N-sulfonic acid sodium salt. Illustrative examples of compounds containing $R^1$ and/or $R^2$ having the formula (2) are N-(dimethoxyphosphino)thienamycin, N-(dibenzyl-oxyphosphino)-thienamycin, N-(dihydroxyphosphino)thienamycin disodium salt, N-(dimethoxyphosphinyl)thienamcyin, N-(dimethoxy-phosphinothioyl)thienamcyin, N-(dibenzyloxy-phosphinyl)thienamycin and N-(dihydroxyphosphinyl)thienamycin disodium salt.

Of particular interest are acyl groups $R^1$ and $R^2$ of Formula II, which are conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxy-carbonyl, trifluoroacetyl, bromoethoxycarbonyl, 9-fluorenylmethoxycarbonyl, dichloroacetyl, 2,2,2-trichloroethoxycarbonyl, bromo-t-butoxycarbonyl, phenoxyacetyl. Non-acyl protective groups such as o-nitrophenylsulphenyl and tri($C_{1-6}$ alkyl)silyl, for example, trimethylsilyl and t-butyldimethylsilyl are also of interest.

The following radicals, according to the foregoing definition of acyl (radicals $R^1$ and $R^2$ of Formula II, above), are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylamino-acetyl, an N,N,N-trimethylammoniumacetyl salt, 3-(N,N-dimethyl)aminopropionyl, a (3-(N,N,N-trimethyl)ammonium propionyl salt, an N,N,N-triethylammoniumacetyl salt, a pyridiniumacetyl salt, guanylthioacetyl, guanidinoacetyl, 3-quanidinopropionyl, $N^3$-methylguanidinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, $N^3$-dimethylaminoacetamidinopropionyl, ureidocarbonyl, dimethylaminoguanylthioacetyl, a 3-(1-methyl-4-pyridinium)propionyl salt, 3-(5-aminoimidazol-1-yl)propionyl, 3-methyl-1-imidazoliumacetyl salt, 3-sydnonylacetyl, o-aminomethylbenzoyl, o-aminobenzyl,

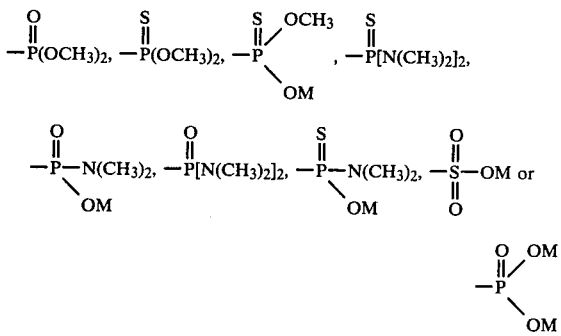

where M is as defined above, and is in particular sodium.

Especially preferred acyl radicals ($R^1$ and $R^2$ of Formula II, above) are terminally substituted acyls in which the substituent is one of certain acidic or basic groups. Such preferred substituted acyls may be represented by the following formula:

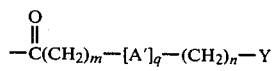

and these radicals and the corresponding radicals in which the

group is omitted are also preferred values of $R^3$. In the formula q is 0 or 1; each of m and n, independently of the other, is 0, 1, 2, 3, 4 or 5; A' is 0, —NR°—(where R° is hydrogen or $C_{1-6}$ alkyl) or S, and Y is an amino or substituted amino radical of formula:

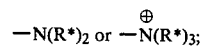

an amidino or substituted amidino radical or formula:

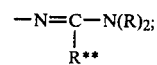

a guanidino or substituted guanidino radical of formula:

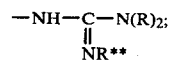

or a guanyl or substituted guanyl radical of formula:

where each R, independently of the other, is hydrogen; $N(R°)_2$ (where R° is hydrogen or $C_{1-6}$ alkyl); $C_{1-6}$ alkyl, $C_{1-6}$ alkoxy; ($C_{1-6}$ alkoxy)—($C_{2-6}$ alkyl), $C_{3-6}$ cycloalkyl or cycloalkyl-($C_{1-3}$ alkyl) or the two R groups are joined to form, together with the N atom to which they are attached, a ring having 3 to 6 atoms; R* is a radical as defined for R except that if cycloalkylalkyl, it must be ($C_{3-6}$ cycloalkyl)-$C_{1-3}$ alkyl; and R** is a radical as defined for R or a ($C_{1-6}$ alkoxy)methyl radical; or Y is a monocyclic or bicyclic heterocyclic aromatic or non-aromatic radical having 4 to 10 nuclear atoms and in which the hetero atom or atoms are nitrogen and optionally oxygen or sulfur.

Such heterocycles are representatively illustrated by the following list of radicals (R' is H or $C_{1-6}$ alkyl):

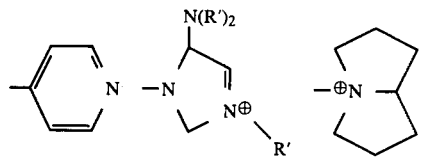

-continued

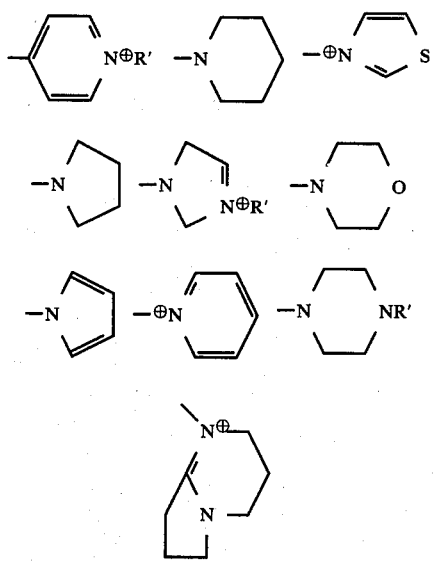

The following additional specific carboxylic acyl radicals are also representative and are preferred: substituted or unsubstituted phthaloyl when $R^1$ and $R^2$ are joined together:

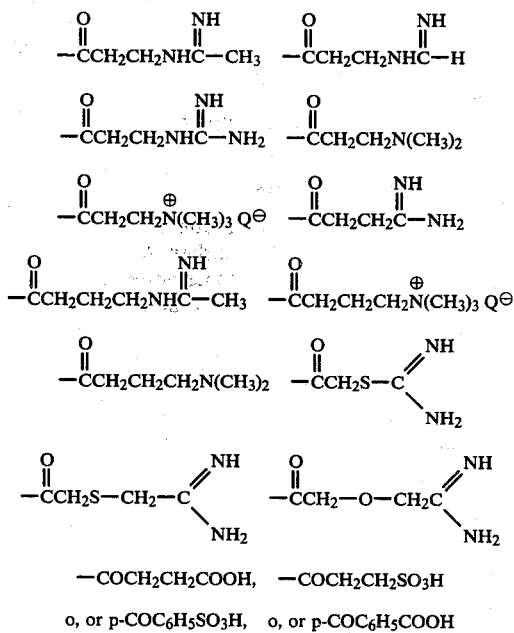

—COCH$_2$CH$_2$COOH, —COCH$_2$CH$_2$SO$_3$H o, or p-COC$_6$H$_5$SO$_3$H,   o, or p-COC$_6$H$_5$COOH where $Q^\ominus$ is an anion.

However, it is to be understood that any acyl radical may be used in the practice of the invention and is to be considered within the scope of the invention.

A of Formula (I) above represents hydrogen; loweralkanoyl especially $C_{1-6}$ alkanoyl such as acetyl, n-propanoyl, or n-butanoyl; or trimethylsilyl, preferably, A is hydrogen, acetyl or trimethylsilyl.

B of Formula (I) above represents hydrocarbyl or substituted hydrocarbyl which can be loweralkyl, loweralkenyl alkyl, alkanoyl, alkanoylalkyl, alkanoyloxyalkyl, alkoxyalkyl, loweralkynyl, aralkyl, aryl, and cycloalkyl, a heterocyclic group, such as heterocyclic alkyl or heterocyclic alkenyl which can also be substituted with one or more groups such as halo (Cl, F, Br, etc.) hydroxy, alkoxy, mercapto, amino, substituted amino, nitro, sulfonyl, sulfinyl, sulfamoyl, alkanoyloxy, carbamoyloxy, carboxy, alkanoyl carboxamido and N-substituted carboxamido. Preferably, B is aralkyl, aryl, straight or branched alkenyl, cycloalkyl, alkanoyl loweralkyl or alkanoyloxy loweralkyl. Representative examples of such groups are $C_{1-6}$alkyl especially methyl, ethyl, isopropyl, isobutyl, or t-butyl, allyl, 3-butenyl, methoxyethyl, benzyl, p-nitrobenzyl, p-sulfonylbenzyl, m-fluorobenzyl, o,p-dinitrobenzyl, o-nitrobenzyl o,p-dichlorobenzyl, p-methylbenzyl, m-methoxybenzyl, o-methylthiobenzyl, benzhydryl, bis(p-methoxy)benzhydryl, triphenylmethyl(trityl), —CH$_2$OCH$_2$OCOt—Bu, —CH$_2$OCOt—Bu, and the like.

Preferably B is substituted or unsubstituted (1) aralkyl, especially aryl, $C_{1-10}$ alkyl such as benzyl, p-nitrobenzyl, phenethyl, p-methoxyphenylpropyl, o,p-dichlorophenyl-n-hexyl, o, p-dinitrobenzyl, benzhydryl or trityl;

(2) lower alkenylalkyl especially (CH$_2$)$_{1-10}$

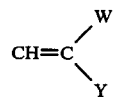

where W and Y independently are hydrogen or $C_{1-6}$ alkyl, for example, CH$_3$—CH=CH$_2$;

(3) straight or branched $C_{1-6}$ alkyl;

(4) straight or branched $C_{2-6}$ alkenyl;

(5) $C_{1-6}$ alkoxycarbonyl $C_{1-10}$ alkyl especially (CH$_2$)$_{1-6}$COOC$_{1-4}$alkyl such as —CH$_2$CH$_2$COOCH$_3$;

(6) alkanoyloxyloweralkyl especially (CH$_2$)$_{1-10}$

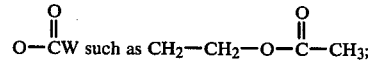

(7) $C_{1-6}$ alkylamido $C_{1-10}$ alkyl especially $C_{1-6}$ alkyl amido $C_{1-4}$ alkyl such as CH$_3$—CONH—CH$_2$CH$_2$—;

(8) alkoxyloweralkyl especially $C_{1-6}$ alkoxy $C_{1-6}$ alkyl such as CH$_3$OCH$_2$CH$_2$;

(9) $C_{1-6}$ alkylaminocarbonyl $C_{1-10}$ alkyl especially $C_{1-4}$ alkylaminocarbonyl $C_{1-6}$ alkyl such as C$_2$H$_5$NHCOCH$_2$CH$_2$—; or

(10) halo loweralkyl especially chloro or fluoro $C_{1-6}$ alkyl such as 2,2,2-trichloroethyl.

Even more preferably, B is substituted or unsubstituted (1) benzyl, p-nitrobenzyl;
(2) benzhydryl or trityl;
(3) ethyl, isopropyl or t-butyl;
(4) —CH$_2$CH$_2$CH=CH$_2$;
(5) allyl;
(6) $C_{1-6}$ alkanoyloxymethyl;
(7) $C_{1-6}$ alkanoylmethyl;
(8) trichloroethyl;
(9) CH$_2$COCH$_2$OCOt-Bu; or
(10) phthalidyl.

The thienamycin esters of structural formula (I) where B is other than hydrogen can be prepared from the acid (where B is H) according to conventional methods of esterification. For example, (I) A thienamycin ester of formula (I) is treated with a lower alkanol, a substituted or unsubstituted benzyl alcohol, or a substituted or unsubstituted benzhydrol (diphenylmethanol) in the presence of a catalyst such as sulfuric acid, hydrochloric acid and any one or a combination of the acid illustrated below in Table I.

TABLE I
Catalyts for Esterification (1) Hydrochloric acid or hydrobromic acid
(2) Sulfuric acid
(3) $C_{1-3}$alkanoic acid e.g. acetic acid
(4) Phosphoric acid
(5) Trifluoroacetic acid or anhydride
(6) Trichloroacetic acid
(7) p-Toluenesulfonic acid or other arylsulfonic acids
(8) Acidic ion-exchange resins with calcium sulfate
(9) Polymer-protected aluminium chloride, e.g., a complex between anhydrous aluminium chloride and polystyrene-divinyl benzene copolymer diphenylphosphitepyridine
(10) A Lewis acid such as boron trifluoride
(11) Aromatic sulfonylchloride-pyridine, e.g., p-toluenesulfonylchloride
(12) triphenylphosphine ditriflate
(13) dicyclohexylcarbodiimide (DCCD)
(14) β-trichloromethyl-β-propiolactone
(15) N,N'-cabonyldimidazole
(16) triphenylphosphinediethylazodicarbonylate
(17) 6-chlorobenzenesulfonyloxybenzotriazole
(18) 1-methyl-2-halopyridinium iodide-tertiary amine (e.g., triethylamine).

The esterification is usually conducted at from about 0° to about 150° C. with or without refluxing until the esterification is substantailly complete. Optionally, a solvent may be used to facilitate the reaction. The common solvents used are benzene, toluene, xylene, sulfolane-xylene, diethylether, tetrahydrofuran, 1,2-dimethoxyethane, dioxane and the like;

(II) A thienamycin ester of formula (I) is converted to an acid halide such as acid chloride or bromide via treatment with a halogenating agent such as thienyl chloride, phosphorus penta- or oxychloride followed by reaction with an appropriate alcohol; and (III) Other methods such as alkylation of carboxylate salts (e.g., K+, Na+, Ca++, Ag+, Cu+, tetralkylammonium-R$_4$N+, and Hg++ salts) of formula (I) with alkyl halides, for example, benzychloride, benzyhydryl chloride; reaction with alkyl isoureas; treatment with diazomethane; alcoholysis of anhydride derived from the cephalosporin acid of formula (I); transformation with alkyl t-butyl ethers; and the like may also be used. These methods are disclosed in Saul Patai, editor, *The Chemistry of Functional Groups*, Supplement B, *The Chemistry of Acid Derivatives*, pp. 441-436, John Wiley & Sons, Chichester-New York-Brisbane-Toronto, 1979, and are incorporated herein by reference.

This invention also relates to a method of treating inflammation in patients using a compound of Formula (I), as the active constituent.

It has been found that the compounds of Formula (I) have anti-inflammatory activity and are effective in the prevention and inhibition of edema and granuloma tissue formation as shown below in Table II by the effective inhibition of the proteolytic function of human granulocyte elastase.

TABLE II

Protocol—Enzyme Assays for the Inhibition of Human Polymorphonuclear Leukocyte Elastase Via Hydrolysis of N-t-Boc-alanyl-alanyl-prolylalanine-p-nitroanilide

Reagents 0.05M TES (N-tris[hydroxymethyl]methyl-2-aminoethanesulfonic acid) Buffer, pH 7.5.

0.2 mM N-t-Boc-alanyl-alanyl-Prolyl-Alanine-p-nitroanilide (Boc-AAPAN).

To prepare substrate, the solid (m.w. 550) was first dissolved in 10.0 ml DMSO. Buffer at pH 7.5 was then added to a final volume of 100 ml.

Crude extract of human polymorphonuclear leukocytes (PMN) containing elastase activity.

Inhibitors (thienamycin esters) to be treated dissolved in DMSO just before use.

Assay Procedure

To 1.0 ml of 0.2 mM Boc-AAPAN in a cuvette, 0.01–0.1 ml of DMSO with or without inhibitor was added. After mixing, a measurement was taken at 410 mµ to detect any spontaneous hydrolysis due to presence of test compound. 0.05 Milliliters of PMN extract was then added and the ΔOD/min at 410 mµ was measured and recorded. Beckman model 35 spectrophotometer was used.

Results

Results were reported as % inhibition produced by test compound within 2 minutes as represented by the % decrease in ΔOD/min as compared to a control without inhibitor.

Comments

The elastase activity in the crude PMN extract may vary from one preparation to another. A control of each new batch is run, and the volume added in the assay procedure is adjusted according to activity.

RESULTS
The following table summarizes the inhibition of PMN elastase by various N—acyl thienamycin esters:

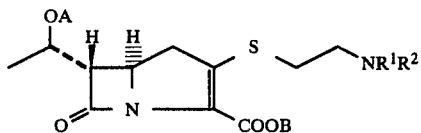

| R$^1$ | R$^2$ | A | B | Conc. of Compound µg/ml | % Inhibition* |
|---|---|---|---|---|---|
| R$^1$ and R$^2$ joined together: | | H | benzyl | 20 | 100 |
| | | | | 5 | 89 |
| phthaloyl | | | | 2 | 56 |
| | | | | 1 | 39 |
| phthaloyl | | H | p-nitrobenzyl (PNB) | 20 | 100 |
| | | | | 5 | 93 |
| | | | | 2 | 86 |
| | | | | 1 | 76 |
| | | | | .5 | 50 |
| —COCH$_2$C$_6$H$_5$ | H | H | PNB | 50 | 100 |
| | | | | 20 | 95 |
| | | | | 5 | 84 |
| | | | | 1 | 47 |
| phthaloyl | | TMS (Tri- | PNB | 50 | 96 |
| | | | | 25 | 95 |

-continued
RESULTS
The following table summarizes the
inhibition of PMN elastase by various N—acyl
thienamycin esters:

$$\text{structure: OA-O-CH(CH_3)-[β-lactam with N]-CH_2-S-CH_2CH_2-NR^1R^2, COOB}$$

| R$^1$ | R$^2$ | A | B | Conc. of Compound μg/ml | % Inhibition* |
|---|---|---|---|---|---|
| | | methyl-silyl) | | 10 | 95 |
| | | | | 2 | 83 |
| | | | | 1 | 38 |
| —COCH$_2$C$_2$H$_5$ | H | Ac | PNB | 50 | 89 |
| | | | | 20 | 69 |
| | | | | 5 | 31 |

*Measured within 2 minutes. See Results, p. 25.

Accordingly, the compounds of Formula (I) can be used to reduce inflammation and relieve pain in diseases such as emphysema, rheumatoid arthritis, osteoarthritis, gout, bronchial inflammation, infectious arthritis, rheumatic fever and the like.

For treatment of inflammation, fever or pain, the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Recent studies indicate that esterification of the carboxyl group of β-lactam antibiotics can improve significantly the oral bioavailability of the parent drug. See W. E. Wright et al., *The Journal of Antibiotics*, XXXII, No. 11, 1155 (1979). Accordingly, esters of the compounds of formula (I) which can be easily hydrolyzed to acids of formula (I) such as acetoxymethyl ester, (5-methyl or alkyl-2-oxo-1,3-dioxolen-4-yl)methyl ester or methoxymethyl ester of compound (I) are prepared for oral formulation. For example, oral solutions or suspensions may be prepared from an acetoxymethyl ester of compound (I) in saline or 50% aqueous propylene glycol.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturallyoccurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional escipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). Preferably, the dosage is from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredient that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

What is claimed is:

1. A method of treating anti-inflammatory conditions comprising the administration to a mammalian species in need of such treatment an effective amount of a compound of formula:

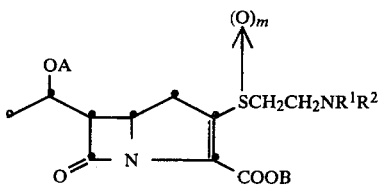

or a non-toxic pharmaceutically acceptable salt thereof; in which m is 0 to 2, $R^1$ and $R^2$ independently are hydrogen, $C_{1-6}$alkyl or an acyl group of the formula

wherein R" represents hydrogen, $C_{1-6}$alkyl, aralkyl, amino, $C_{1-6}$alkylamino, di($C_{1-6}$alkyl)amino, alkylthio, alkoxy, aryloxy, alkenyl, alkynyl, aryl, cycloalkyl, or $R^1$ and $R^2$ joined together to form a phthaloyl group; A is hydrogen, loweralkyl or trimethylsilyl; and B is
  (1) straight or branched loweralkyl;
  (2) straight or branched loweralkenyl;
  (3) loweralkynyl;
  (4) cycloalkyl;
  (5) aryl;
  (6) aralkyl;
  (7) alkanoylalkyl;
  (8) alkanoyloxyalkyl;
  (9) alkanoyl; or
  (10) alkoxyalkyl;
groups (1) to (10) above being unsubstituted or substituted with one or more groups selected from the group consisting of:
  (a) halo;
  (b) hydroxyl;
  (c) alkoxy;
  (d) mercapto;
  (e) amino;
  (f) substituted amino;
  (g) nitro;
  (h) sulfonyl;
  (i) sulfinyl;
  (j) sulfamoyl;
  (k) alkanoyloxyl;
  (l) carbamoyloxyl
  (m) carboxy;
  (n) alkanoyl;
  (o) carboxamido; and
  (p) N-substituted carboxamido.

2. The method according to claim 1 wherein $R^1$ and $R^2$ joined together form substituted or unsubstituted phthaloyl.

3. The method according to claim 2 wherein A is hydrogen, acetyl, or trimethylsilyl, and B is substituted or unsubstituted
  (1) aralkyl;
  (2) lower alkenylalkyl;
  (3) straight or branched $C_{1-6}$ alkyl;
  (4) straight or branched $C_{2-6}$ alkenyl;
  (5) $C_{1-6}$ alkoxycarbonyl $C_{1-10}$ alkyl;
  (6) alkanoyloxyloweralkyl;
  (7) $C_{1-6}$ alkylamido $C_{1-10}$ alkyl;
  (8) alkoxyloweralkyl;

(9) C$_{1-6}$ alkylaminocarbonyl C$_{1-10}$ alkyl; or
(10) halo loweralkyl.

4. The method according to claim 2 wherein B is substituted or unsubstituted
(1) benzyl, o or p-dinitrobenzyl;
(2) benzhydryl or trityl;
(3) ethyl, isopropyl or t-butyl;
(4) —CH$_2$CH$_2$CH=CH$_2$;
(5) allyl;
(6) C$_{1-6}$ alkanoyloxymethyl;
(7) C$_{1-6}$ alkanoylmethyl;
(8) trichloroethyl;
(9) CH$_2$COCH$_2$OCOt-Bu; or
(10) phthaloyl.

5. The method of claim 1 which is:
(a) benzyl ester of N-phthaloyl thienamycin;
(b) p-nitrobenzyl ester of N-phthaloyl thienamycin;
(c) p-nitrobenzyl ester of N-benzylcarbonyl thienamycin;
(d) p-nitrobenzyl ester of O-acetyl-N-benzylcarbonyl thienamycin; or
(e) p-nitrobenzyl ester of O-trimethylsilyl-N-phthaloyl thienamycin.

* * * * *